United States Patent
Morath et al.

(10) Patent No.: US 11,554,139 B2
(45) Date of Patent: Jan. 17, 2023

(54) MIC THERAPY FOR SPECIFIC IMMUNOSUPPRESSION IN TRANSPLANTATION

(71) Applicants: TOLEROGENIXX GMBH, Heidelberg (DE); UNIVERSITÄT HEIDELBERG, Heidelberg (DE)

(72) Inventors: Christian Morath, Heidelberg (DE); Anita Schmitt, Bammental (DE); Matthias Schaier, Heidelberg (DE); Gerhard Opelz, Heidelberg (DE); Peter Terness, Eppelheim (DE); Christian Kleist, Neckargemünd (DE); Volker Daniel, Heidelberg (DE); Caner Süsal, Dossenheim (DE); Michael Schmitt, Bammental (DE); Martin Zeier, Gaiberg (DE)

(73) Assignees: TOLEROGENIXX GMBH, Heidelberg (DE); UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 17/269,027

(22) PCT Filed: May 17, 2019

(86) PCT No.: PCT/EP2019/062857
§ 371 (c)(1),
(2) Date: Feb. 17, 2021

(87) PCT Pub. No.: WO2020/233776
PCT Pub. Date: Nov. 26, 2020

(65) Prior Publication Data
US 2022/0118009 A1  Apr. 21, 2022

(51) Int. Cl.
| | |
|---|---|
| A61K 35/15 | (2015.01) |
| A61P 37/06 | (2006.01) |
| A61K 31/164 | (2006.01) |
| A61K 31/405 | (2006.01) |
| A61K 31/407 | (2006.01) |
| A61K 31/422 | (2006.01) |
| A61K 31/706 | (2006.01) |

(52) U.S. Cl.
CPC ............ *A61K 35/15* (2013.01); *A61K 31/164* (2013.01); *A61K 31/405* (2013.01); *A61K 31/407* (2013.01); *A61K 31/422* (2013.01); *A61K 31/706* (2013.01); *A61P 37/06* (2018.01)

(58) Field of Classification Search
None
See application file for complete search history.

(56) References Cited

U.S. PATENT DOCUMENTS

| | | | |
|---|---|---|---|
| 2011/0223145 A1* | 9/2011 | Terness | C12N 5/0634 424/93.71 |
| 2018/0057792 A1 | 3/2018 | Feskov et al. | |

FOREIGN PATENT DOCUMENTS

WO  2010/000730 A1  1/2010

OTHER PUBLICATIONS

Morath et al., Pediatr Nephrol. Feb. 2018;33(2):199-213 (Year: 2018).*
International Search Report and Written Opinion dated Feb. 28, 2020 for corresponding PCT Application No. PCT/EP2019/062857.
Kleist, C. et al., "Generation of suppressive blood cells for control of allograft rejection," Clinical Science, vol. 128, No. 9, 2015, pp. 593-607 XP9518562.
Jiga, L. P. et al., "Inhibition of Heart Allograft Rejection With Mitomycin C-Treated Donor Dendritic Cells," Transplantation, vol. 83, No. 3, 2007, pp. 347-350 XP009123859.
Ehser, S. et al., "Suppressive dendritic cells as a tool for controlling allograft rejection in organ transplantation: Promises and difficulties," Human Immunology, vol. 69, No. 3, 2008, pp. 165-173 XP022589354.
Yamazaki, H. et al., "Successful treatment of recurrent chronic myelogenous leukemia in allogeneic marrow transplant recipient with the donor leukocyte transfusion, without induction of acute graft-versus-host disease," Japanese Journal of Clinical Hematology, vol. 36, No. 7, 1995, pp. 677-681 XP009518594.

* cited by examiner

*Primary Examiner* — Daniel C Gamett
(74) *Attorney, Agent, or Firm* — Polsinelli PC

(57) ABSTRACT

The present invention relates to pharmaceutical compositions with isolated and treated whole blood cells or Peripheral Blood Mononuclear Cells (PBMCs) as well as such pharmaceutical compositions for use in the prevention and/or treatment of organ or cell graft rejection in a human graft recipient.

10 Claims, 10 Drawing Sheets

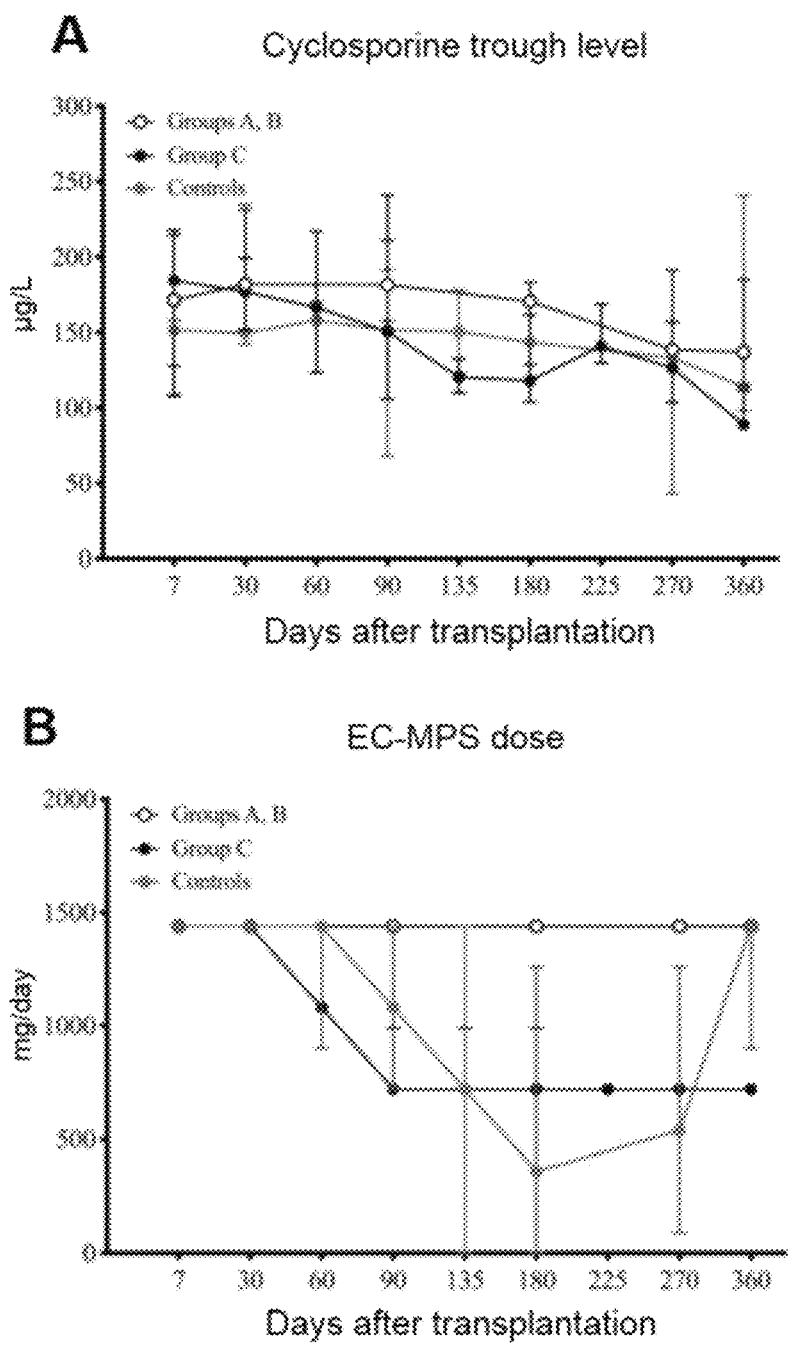
FIG. 2 (a, b)

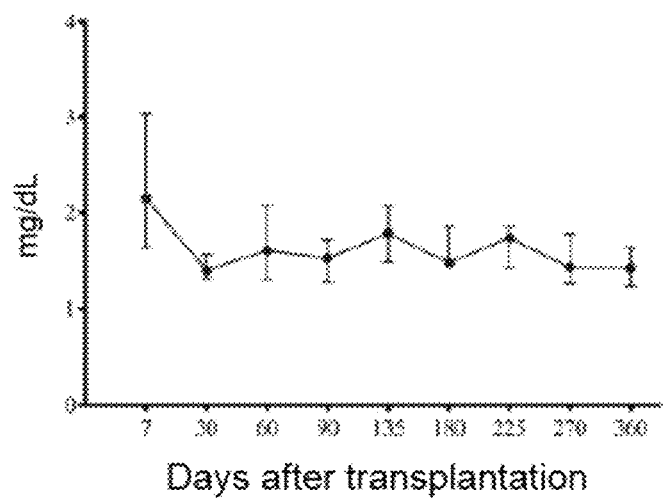
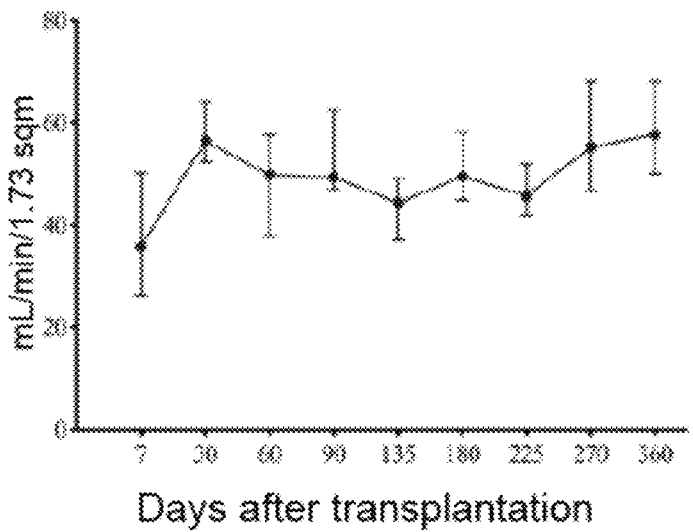
FIG. 3 (a,b)

MIC THERAPY FOR SPECIFIC IMMUNOSUPPRESSION IN TRANSPLANTATION

CROSS-REFERENCE TO RELATED APPLICATIONS

This application is a national stage application (under 35 U.S.C. § 371) of PCT/EP2019/062857, filed May 17, 2019, which is incorporated herein by reference in its entirety.

The present invention relates to pharmaceutical compositions with isolated and treated whole blood cells or Peripheral Blood Mononuclear Cells (PBMCs) as well as such pharmaceutical compositions for use in the prevention and/or treatment of solid organ or cell graft rejection in a human graft recipient.

Due to a variety of diseases or accidents or many other reasons, patients and injured people are in need of replacement of their organs by organ transplantations. According to the Global Observatory on Donation and Transplantation (http://www.transplant-observatory.org/), a total number of 135,860 organs were transplanted worldwide in 2016. The number of patients in need thereof and currently placed on a waiting list, however, is far more. In addition to the comparably low number of organ donors, the donated organs and the recipients also have to be matched to reduce the risk for a rejection by the recipient's immune system and thus to increase the chance and duration of the functionality of the transplanted organ.

The mammalian, in particular human, immune system must differentiate between self and non-self and recognize as well as fight all non-self material which may be a harm to the organism. In addition to the recognition of cells or other parts such as nucleic acids of a non-self organism as e.g. from bacteria or viruses, the immune system also recognizes (and has to recognize) cells or other parts from a non-self organism belonging to the same species. This aspect is one of the major drawbacks in medical organ or cell transplantation, as typically, the recipient's immune system will recognize the transplanted organ or cells as non-self and attack and destroy the transplanted organ or cells. This natural, defensive mechanism of the mammalian, particularly human, organism is one of the main reasons for unsuccessful transplantations or for a vanishing functionality of the transplanted organ over time. To reduce the risk for a patient mediated by the immune system's ability to recognize and attack a transplant, usually a donor and a recipient with similar cellular patterns serving as distinguishing feature of self and non-self are selected. Such a match of donor and recipient is often, but not necessarily, achieved in close relatives.

However, as these distinguishing features are still different even in closest relatives, such a match is not sufficient to prevent an immune response against a transplant. Thus, it is a required and standard approach to further suppress the recipient's immune system to strongly reduce the risk of an immune response towards the transplant.

Typically, the endogenous immune system is thus broadly and unspecifically suppressed so that the transplant is not attacked by the immune response and may survive and operate over a long time in the recipient's body and to avoid an excessive and dangerous inflammatory response for the patient.

The present state of the art for such a treatment of post-transplant patients is concurrent treatment with a number of drugs that weaken the patient's immune system in a non-specific manner. For example, the current established treatment for kidney transplants is multiple immunosuppression comprising antibody induction therapy, calcineurin inhibitors (e.g. Cyclosporin A, Sandimmun®), cell proliferation inhibitors (e.g. mycophenolic acid, MPA derivatives) and corticosteroids (Ekberg H et al., NEJM 2007).

Transplant recipients are thus usually dependent on immune suppression during the rest of their lives. One of the major disadvantages of such a treatment is that the immune system as such is suppressed, as described above. Thus, the recipient's immune system is also suppressed for any other non-self organism, cell or other material. Recipients are therefore at high risk for any infectious diseases. Furthermore, the side effects of a suppressed immune system particularly include impaired wound healing, an increased risk of tumour diseases and a significant increase in the risk of cardiovascular diseases (Morath C et al., JASN 2004, Opelz G et al., AJT 2013).

Moreover, another problem of current immunosuppression in transplant recipients is a "limited" effectiveness: it is known that, despite long-term intensive immunosuppression, more than half of the patients suffer from chronic rejection and the long-term loss of the transplant (Sellares J et al., AJT 2012).

To date, transplant recipients are bound to immunosuppression for a lifetime and with all its disadvantages with, nevertheless, a risk that a chronic rejection may still occur.

The primary object of the present invention was thus to provide an improved prevention and/or treatment of organ or cell graft rejection in a human graft recipient, with which the disadvantages of the current options are overcome or at least reduced.

The primary object of the present invention is achieved by a pharmaceutical composition comprising or consisting of
  a) isolated whole blood cells and/or Peripheral Blood Mononuclear Cells (PBMCs) treated with a therapeutically effective amount of an active substance, and
  b) optionally a pharmaceutically acceptable carrier,
  for use in the prevention and/or treatment of organ or cell graft rejection in a human graft recipient, wherein the isolated whole blood cells or PBMCs are obtained or derived from the graft donor,
  wherein the prevention and/or treatment of organ or cell graft rejection comprises administering the pharmaceutical composition to the recipient, wherein the amount of the pharmaceutical composition is selected such that at least $0.25 \times 10^6$ cells, preferably at least $1.5 \times 10^6$ cells of the treated whole blood cells or the treated PBMCs per kg body weight of the recipient are administered, preferably in one administration step,
  wherein the active substance comprises or consists of one or more substances selected from the group consisting of chemotherapeutics, proteasome inhibitors, immunosuppressive agents and anti-proliferative substances.

Developing an alternative to unspecific immunosuppression is intended to be a curative and not a symptomatic treatment. The aim is to influence the immune system in such way that it is still able to defend against bacteria, viruses, tumour cells etc., but unwanted reactions of the immune system, e. g. against foreign donor characteristics, can be specifically switched off. By treating blood cells, e.g. monocytes with active substances, e.g. mitomycin C (mitomycin C-treated peripheral blood mononuclear cells=modified immune cells=MICs), they do not turn into stimulatory but rather into suppressive cells similar to myeloid-derived suppressor cells (MDSCs) from cancer patients.

It has been described in WO 2010/000730 that a pharmaceutical composition comprising isolated blood cells treated with a therapeutically effective amount of a chemotherapeutic agent may be used to provide and achieve a tailored or targeted immunosuppression in an autoimmune disease setting. Once the active substance has been washed out, where applicable, the MICs are reinfused into the body of the transplant recipient. WO 2010/000730 thus specifically discloses a specific treatment for a multiple sclerosis model in mice (experimental autoimmune encephalitis (EAE) mouse model) for a highly specific setting concerning the dosage regimen to be applied in the murine model, more particularly for an EAE autoimmune model.

The standard procedure as previously used consists of applying immunosuppressive medication that leads to a general weakening of the immune system and the associated side effects. Such a harsh treatment with a chemical immunosuppressive agent will no longer be necessary applying the teaching of the present invention, as the amount of immunosuppressive medication can be reduced to a minimum or is no longer necessary at all in patients treated with a pharmaceutical composition according to the invention.

The invention offers tailor-made, patient-specific immunosuppression that tackles the causes and is free from side effects, thereby setting itself significantly apart from presently available treatment methods. The cell therapy can be manufactured centrally in a standard form for the individual indications; the individual component is achieved by the donor blood cells, and there is no need for expensive customisation. The method is easy to implement in routine clinical practice, as it uses existing structures, and hospitals do not have to commit to expensive investments in special laboratories. Finally, treatment costs are significantly reduced, as the life-long treatment with medication is no longer required, or is considerably reduced.

Treatment or prevention of a rejection by MIC administration has superior or at least equivalent efficacy compared to the gold standard of multi-drug immunosuppression while at the same time the side effects are reduced. It is thus an enormous benefit for the patients with great economic perspectives.

A special treatment, i.e. in particular a specific dosage regimen, has an outstanding importance for providing an optimised therapy. On the one side, the mammalian, particularly human, immune system is tightly regulated and a suppressive effect of the immune system will also be evoked by low doses of administered treated whole blood cells or the treated PBMCs. However, it is assumed that in this case more time is required to achieve and settle a comprehensive and long-lasting targeted suppression of the immune system. Thus, a higher dose is expected to provide the tailored immunosuppression within shorter time.

On the other side, increasing the dose may also reach a limit as with higher doses the risk for e.g. evoking a thrombosis or embolism increases. As these side-effects are surely to be avoided, critical attention is to be raised on the particular dosage regimen. It is to be noted, however, that the tailored suppression of the immune system is also achieved with such high doses, yet when concerning a possible treatment option for human graft recipients, this factor should also be considered.

It was surprisingly found that a dosage regimen of the treated cells, as described above, of at least $0.25 \times 10^6$ cells per kg body weight, preferably at least $1.5 \times 10^6$ cells per kg body weight of the human graft recipient showed a stable graft function, survival of the graft and patient and no rejection or side-effects related to the treatment (cf. example 1).

The terms "patient", "subject", "recipient" or "graft recipient" as used herein may be used interchangeably and describe a patient in need of or planned to receive an organ or cell graft transplantation as well as a patient having already received such a graft, wherein the transplantation may even have occurred months, years or decades ago.

The term "donor" as used herein preferably describes a person donating whole blood cells. This person, whether a living donor or a dead donor, may be the donor of the transplanted organ. In some cases, however, a patient may also be a donor.

The term "isolated whole blood cells" preferably describes cells obtained from a blood sample or from splenetic cells. The blood cells can be obtained by drawing blood from a donor, optionally including leukapheresis. Furthermore, the blood cells may also be isolated from splenetic cells. Particularly preferably, the term "isolated whole blood cells" describes white blood cells which are obtained by leukapheresis as described above or which are further isolated from the blood cells obtained as described above, with methods well-known to a skilled person.

The term "PBMCs" or "Peripheral Blood Mononuclear Cells" describe a distinct cell type of peripheral blood cells with one round nucleus, such as lymphocytes, monocytes or dendritic cells. PBMCs can be extracted from whole blood using ficoll, a hydrophilic polysaccharide that separates layers of blood, with monocytes and lymphocytes forming a buffy coat under a layer of plasma. This buffy coat contains the PBMCs. Additionally, PBMC can be extracted from whole blood using a hypotonic lysis which will preferentially lyse red blood cells. This method typically results in neutrophils and other polymorphonuclear (PMN) cells. Furthermore, PBMCs can also be obtained from whole blood by leukapheresis. This method typically results in PBMCs, PMNs, some erythrocytes and platelets.

Preferably, the PBMCs comprise or consist of monocytes and lymphocytes.

Typically, the isolated whole blood cells and/or PBMCs are obtained from the donor by collecting a blood sample, optionally including leukapheresis. In some cases, the leukapheresis product may also be treated with ficoll.

Additionally or alternatively, these cells are derived from the donor, e.g. by targeted differentiation of stem cells obtained from the donor. Usually, such cells are obtained or derived from one donor. However, two or more donors may also be possible. In this case, the term "donor" may include one, two, several or all donors.

Generally, it is preferred that the cells are produced under Good Manufacturing Practice (GMP) conditions.

Typically, the number of cells is measured by manual or automated cell counting. The cell counting is preferably performed with a dye for live/dead staining so that the amount of viable cells can be determined. Furthermore, the composition of the cells in the product is analysed by flow cytometry. Preferably, the pharmaceutical composition contains monocytes, lymphocytes and a lower amount of granulocytes, platelets and erythrocytes.

The term "cells treated with" as used herein preferably describes a treatment according to the following procedure: Cells are obtained as described above and washed. Subsequently, the active agent, is added to the cells ($10^6$ cells/ml) to obtain a concentration of 10-100 µg/ml and for 30 min. Afterwards, the cells are extensively washed to remove the active agent. Typically, the cells are administered, as described herein, after 4 to 48 hours after the treatment as described above.

Preferably, the treatment of the cells, as described above, is performed via the following procedure:

First, the obtained cells are carefully washed with a washing buffer. Then, a buffer is added to the reconstituted active agent(s) in a proportion of about 4:1. Thereafter, the mixture of buffer and active agent(s) is added to the cells ($10^6$-$10^9$ cells/ml) to obtain a concentration of 10-105 μg/ml. After an incubation time of 30 min at 37° C., the cells are centrifuged carefully. Afterwards, the cells are extensively washed to remove the active agent(s). For the quality control, the final product is tested for cell count, viability and composition of cells by flow cytometry, for sterility by the direct inoculation method according to Ph. Eur. 2.6.1, for freedom of endotoxins by the limulus amoebocyte lysate test according to Pharm Eur 2.6.14 and for quantification of the washed-out active agent(s) by high performance liquid chromatography. Additionally, according to the respective guidelines, infectious disease markers are tested from donor blood samples.

The term "active substance" describes any substance or combination of substances which consists of or at least comprises one or more substances selected from the group consisting of chemotherapeutics, proteasome inhibitors, immunosuppressive agents, anti-proliferative substances and combinations thereof. Thus, the active substance(s) can be one, two, three, four, five or more different substance(s).

Preferably, the, one, two, three or more or all of the active substances is/are (a) chemotherapeutic(s) selected from the group consisting of alkylating agents (such as busulfan, caroplatin, carmustine, chlorambucil, cisplatin, cyclophosphamide (such as cytoxan), dacarbazine, ifosfamide, lomustine, mecholarethamine, melphalan, procarbazine, streptozocin, and thiotepa), anti-neoplastic antibiotics (such as bleomycin, dactinomycin, daunorubicin, doxorubicin, idarubicin, mitomycin (such as mitomycin C), mitoxantrone, pentostatin, and plicamycin), antimetabolites (such as fluorodeoxyuridine, cladribine, cytarabine, floxuridine, fludarabine, flurouracil (such as 5-fluorouracil (5FU)), gemcitabine, hydroxyurea, mercaptopurine, methotrexate, and thioguanine), calcineurin-inhibitors (such as ciclosporin, tacrolimus), methotrexat, azathioprin, mTOR inhibitors (such as everolimus, sirolimus), costimulator blockade (such as abatacept), JAK inhibitors (such as ruxolitinib) and natural source derivatives (such as mycophenolate (mofetil), docetaxel, etoposide, irinotecan, taxanes (e.g. paclitaxel), teniposide, topotecan, vinblastine, vincristine, vinorelbine, steroids (e.g. glucocorticoids such as prednisone), and tamoxifen).

Preferably, the, one, two, three or more or all of the active substances is/are (a) proteasome inhibitor(s) selected from the group consisting of bortezomib (e.g. Velcade®), carfilzomib (e.g. Kyprolis®) and ixazomib (e.g. Ninlaro®).

Preferably, the, one, two, three or more or all of the active substances is/are (a) immunosuppressive agent(s) selected from the group consisting of mycophenolic acid, mTOR inhibitors, azathioprine, tacrolimus and cyclosporine.

Preferably, the, one, two, three or more or all of the active substances is/are (a) anti-proliferative substance(s) selected from the group consisting of mycophenolic acid, azathioprine, cyclophosphamide, mTOR inhibitors.

It is particularly preferred that the active substance comprises or consists of one or more substances selected from the group consisting of mitomycin C, C2 ceramide, tunicamycin, mycophenolate-mofetil, tryptophan metabolites (such as kynurenines, e.g. Tranilast) and semisynthetic derivatives thereof.

It is especially preferred that the active substance comprises or consists of tryptophan metabolites (such as kynurenines, e.g. Tranilast) and/or mitomycin C.

As used herein, "therapeutically effective amount" means a sufficient amount of said compound to treat a particular disease, at a reasonable benefit/risk ratio. In general, the term "therapeutically effective amount" shall refer to an amount of said compound which is physiologically significant and improves an individual's health. An agent, i.e. said compound, is physiologically significant if its presence results in a change in the physiology of the recipient human. For example, in the treatment of a pathological condition, administration of said compound which relieves or arrests further progress of the condition would be considered both physiologically significant and therapeutically effective.

The terms "treating" or "treatment" of organ or cell graft rejection as used herein is preferably to be understood as a suppression of the rejection so far that the transplanted organ(s) and/or cells remain(s) functional.

The terms "preventing" or "prevention" of organ or cell graft rejection as used herein is preferably to be understood as inhibiting or at least reducing the strength of such a rejection as described herein for a certain period of time in a subject. It will be understood that said period of time is dependent on the amount of the composition according to the invention which has been administered and individual factors of the subject such as the severity of the disorder, the age, body weight, general health, sex and diet of the patient, the time of administration, route of administration, the duration of the treatment as well as drugs used in combination or coincidental with the treatment. Such a prevention only requires the suppression of relatively few and inactive immune cells. In the naïve unstimulated state, a frequency of about one precursor clone in 100,000 $CD8^+$ T cells had been estimated to exhibit specificity for a defined antigen (Blattmann et at., 2002, J. Exp. Med., 195:657-664).

In an acute organ graft rejection, the immune cell clones which recognize tissue of the donor have already expanded. Regarding viral infections, within 7-8 days a massive increase in number of specific T-cell clones occurs, up to 50,000-fold comprising about 15 to 20 proliferation cycles (Williams & Bevan, 2007, Ann. Rev. Immunol., 25:171-192). Thus, the activity of a large number of cells has to be suppressed successfully. Moreover, active immune cells are in a different physiological state as compared to resting immune cells. In order to initiate proliferation and various effector functions naive $CD4^+$ and $CD8^+$ T cells need to encounter antigens in lymphoid organs presented by antigen-presenting cells (APCs). In contrast activated and expanded T cells swarm to the peripheral tissues to find and subsequently eliminate the antigenic sources. During this extremely complex procedure, the activated cells express a mixture of various signaling and effector molecules such as cytokines and chemokines that exhibit uncounted functions upon immune as well as non-immune cells. The exposure to foreign antigens usually results in the appearance of long-lived so-called memory cells making up 5%-10% of the original number of activated effector cells. The quality of the memory cells is reflected by a faster and more effective response to further encounters with the same antigens (Harty & Badovinac, 2008, Nat. Rev. Immunol., 8:107-119; Williams & Bevan, 2007, Ann. Rev. Immunol., 25:171-192; Sprent & Surh, 2002, Ann. Rev. Immunol., 20:551-579; Rogers et at., 2000, J. Immunol., 164:2338-2346. Therefore, the efficacy of the pharmaceutical composition of the present invention for the treatment of an organ graft rejection was surprising.

It is to be understood, however, that such a treatment and/or prevention may not be effective in all subjects treated with the composition according to the present invention. However, the term requires that a statistically significant portion of subjects of a cohort or population are effectively prevented from or at least show a reduction in the strength of organ or cell graft rejection or its accompanying symptoms. Preferably, a cohort or population of subjects is envisaged in this context which normally, i.e. without preventive measures according to the present invention, would develop a (stronger) organ or cell graft rejection.

Additionally or alternatively, the prevalence of such a rejection in a cohort of subjects which have received the composition according to the invention in a manner according to the invention will be significantly lower than the normal prevalence in a cohort of subjects which have not received the composition according to the invention or not in a manner according to the invention. Whether a portion is statistically significant can be determined without further ado by the person skilled in the art using various well known statistic evaluation tools, e.g. determination of confidence intervals, p-value determination, Student's s t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment and/or prevention shall be effective for at least 60%, at least 70%, at least 80%, or at least 90% of the subjects of a given cohort or population.

As immunosuppressants, the pre-treated isolated whole blood cells or PBMCs of the present invention in the specific dosage regimen as disclosed herein are highly useful when administered for the prevention of immune-mediated cell, tissue or organ graft rejection. Examples of transplanted cells, tissues and organs which suffer from these effects are heart, kidney, liver, bone marrow, skin, cornea, lung, pancreas, limb, muscle, nerves, duodenum, small and large intestine, pancreatic-islet-cells, allogeneic hematopoietic stem cells, chimeric antigen receptor T cells, donor lymphocyte infusions, allogeneic hematopoietic stem cells or composites (such as (parts of) the face or the uterus), allogeneic chimeric antigen receptor T cells, and the like.

Preferably, treatment of the rejection of the following organs, cells and tissues is encompassed by the present invention: heart, kidney, liver, bone marrow, skin, cornea, lung, pancreas, limb, muscle, nerves, duodenum, small and large intestine, pancreatic-islet-cells, allogeneic hematopoietic stem cells, chimeric antigen receptor T cells, donor lymphocyte infusions, allogeneic hematopoietic stem cells or composites (such as (parts of) the face or the uterus), allogeneic chimeric antigen receptor T cells, and the like.

Preferably, the pharmaceutical composition according to the invention may also be used in the treatment and/or prevention of graft versus host disease.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, phosphate buffer solutions; non-toxic, compatible lubricants such as sodium lauryl sulfate and magnesium stearate; as well as coloring agents, releasing agents, coating agents, sweetening, flavoring and perfuming agents. Preservatives and antioxidants can also be present in the composition, according to the judgment of the formulator.

The composition according to the present invention may be administered orally, rectally, parenterally, intracisternally, intravaginally, intraperitoneally, bucally, or as an oral or nasal spray. The term "parenteral" as used herein refers to modes of administration which include intravenous, intramuscular, intraperitoneal, intrasternal, subcutaneous and intraarticular injection, preferably as an infusion. Preferably, the administration occurs intravenously, intramuscularly or subcutaneously, preferably as an infusion.

Pharmaceutical compositions of this invention for parenteral injection preferably comprise pharmaceutically-acceptable sterile aqueous or non-aqueous solutions, dispersions, suspensions or emulsions, as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

As described above, a higher dose of the administered cells is expected to provide the tailored immunosuppression within shorter time. Thus, it is preferred that the prevention and/or treatment of organ or cell graft rejection comprises administering to the recipient at least $5\times10^6$ cells, at least $1\times10^7$ cells, at least $5\times10^7$ cells, at least $1\times10^8$ cells or at least $1.5\times10^8$ cells of the treated whole blood cells or the treated PBMCs per kg body weight of the recipient.

To avoid or reduce the risk for e.g. evoking a thrombosis or embolism as described above, it is however preferred that the amount of the pharmaceutical composition is selected such that a maximum of $1\times10^{12}$ cells of the treated whole blood cells or the treated PBMCs per kg body weight of the recipient are administered.

It is preferred that the administration of the pharmaceutical composition is performed in one administration step, however, two, three or more administration steps are also possible.

In addition or as an alternative to the cell number, the time point(s) of the administration steps is/are important for allowing the immune system to develop an efficient/sufficient tailored/targeted suppression. Thus, it is preferred that the cells are administered to the recipient at least 1 day before the transplantation, preferably at least 2 days, at least 3 days, at least 4 days, at least 5 days, at least 6 days, at least 7 days, at least 8 days, at least 9 days, at least 10 days, at least 14 days, at least 21 days or at least 28 days before the transplantation.

The skilled person will be well aware of the fact that the specific combination of cell number and time of application may depend on several individual factors of the subject such as the severity of the disorder, the age, body weight, general health, sex and diet of the patient, route of administration, the duration of the treatment as well as drugs used in combination or coincidental with the treatment or may depend on the organ to be transplanted.

It is known that CD19$^+$CD24$^{high}$CD38$^{high}$ Bregs play an important role in maintaining long-term allograft function and promoting transplant tolerance (Newell K A et al., J Clin Invest 2010; Silva H M et al., Mol Med 2012; Chesneau M et al., Am J Transplant 2014; Shabir S et al., Am J Transplant 2015; Tebbe B et al., PLoS One 2016; Svachova V et al., Transpl Int 2016). Tebbe et al. found in patients receiving routine doses of immunosuppression (with CyA as a calcineurin inhibitor) CD19$^+$CD24$^{high}$CD38$^{high}$ transitional B lymphocyte frequencies in the range of 0-5% during the first year after transplantation (Tebbe B, PIs one 2016). Those patients who showed frequencies greater than 1% showed no rejection episodes.

It was surprisingly found that a treatment with the specific cells disclosed herein using a dosage regimen of at least 1×10$^8$ cells, preferably at least 1.5×10$^8$ cells per kg body weight of the recipient at least 5 days, preferably at least 6 days, particularly preferably at least 7 days before the transplantation leads to a sharp increase of the amount of CD19$^+$CD24$^{high}$CD38$^{high}$ Bregs and thus makes the treatment even much more effective. This correlation was not yet known to date, let alone that there is a correlation at all. The Breg frequencies of transplanted controls who were not subjected to MIC conditioning were comparable to the rates described by Tebbe et al., whereas the patients subjected to such a special treatment showed frequencies in the range of even 5-40% on day 180 after transplantation, exceeding by far the values of controls (median 1%) and those found in these patients before transplantation (cf. example 1 and FIGS. 3 and 4).

Thus, it is preferred that the prevention and/or treatment of organ or cell graft rejection comprises administering to the recipient at least 1×10$^8$ cells, preferably at least 1.3×10$^8$ cells, particularly preferably at least 1.5×10$^8$ cells of the treated whole blood cells or the treated PBMCs per kg body weight of the recipient, wherein the administration is performed at least 5 days, preferably at least 6 days, particularly preferably at least 7 days before the transplantation.

It is particularly preferred that the prevention and/or treatment of organ or cell graft rejection comprises administering to the recipient 1×10$^8$ to 1×10$^{12}$ cells of the treated whole blood cells or the treated PBMCs per kg body weight of the recipient, wherein the administration is performed at least 5 days before the transplantation.

It is particularly preferred that the prevention and/or treatment of organ or cell graft rejection comprises administering to the recipient at least 1×10$^8$ to 1×10$^{12}$ cells of the treated whole blood cells or the treated PBMCs per kg body weight of the recipient, wherein the administration is performed at least 6 days before the transplantation.

It is particularly preferred that the prevention and/or treatment of organ or cell graft rejection comprises administering to the recipient at least 1×10$^8$ to 1×10$^{12}$ cells of the treated whole blood cells or the treated PBMCs per kg body weight of the recipient, wherein the administration is performed at least 7 days before the transplantation.

It is particularly preferred that the prevention and/or treatment of organ or cell graft rejection comprises administering to the recipient at least 1.3×10$^8$ to 1×10$^{12}$ cells of the treated whole blood cells or the treated PBMCs per kg body weight of the recipient, wherein the administration is performed at least 5 days before the transplantation.

It is particularly preferred that the prevention and/or treatment of organ or cell graft rejection comprises administering to the recipient at least 1.3×10$^8$ to 1×10$^{12}$ cells of the treated whole blood cells or the treated PBMCs per kg body weight of the recipient, wherein the administration is performed at least 6 days before the transplantation.

It is particularly preferred that the prevention and/or treatment of organ or cell graft rejection comprises administering to the recipient at least 1.3×10$^8$ to 1×10$^{12}$ cells of the treated whole blood cells or the treated PBMCs per kg body weight of the recipient, wherein the administration is performed at least 7 days before the transplantation.

It is particularly preferred that the prevention and/or treatment of organ or cell graft rejection comprises administering to the recipient at least 1.5×10$^8$ to 1×10$^{12}$ cells of the treated whole blood cells or the treated PBMCs per kg body weight of the recipient, wherein the administration is performed at least 5 days before the transplantation.

It is particularly preferred that the prevention and/or treatment of organ or cell graft rejection comprises administering to the recipient at least 1.5×10$^8$ to 1×10$^{12}$ cells of the treated whole blood cells or the treated PBMCs per kg body weight of the recipient, wherein the administration is performed at least 6 days before the transplantation.

It is particularly preferred that the prevention and/or treatment of organ or cell graft rejection comprises administering to the recipient at least 1.5×10$^8$ to 1×10$^{12}$ cells of the treated whole blood cells or the treated PBMCs per kg body weight of the recipient, wherein the administration is performed at least 7 days before the transplantation.

Furthermore, it is particularly preferred that in this special treatment, the active substance comprises or consists of mitomycin C.

Everything that was said herein with regard to the pharmaceutical composition for use also applies for the pharmaceutical composition independent of its use.

Therefore, another aspect of the present invention relates to a pharmaceutical composition comprising or consisting of
a) isolated whole blood cells or Peripheral Blood Mononuclear Cells (PBMCs) treated with a therapeutically effective amount of an active substance, and
b) optionally a pharmaceutically acceptable carrier,
wherein the composition is suitable for preventing or treating organ or cell graft rejection in a human graft recipient, wherein the isolated whole blood cells or PBMCs are obtained or derived from the graft donor,
characterized in that
the total amount of the treated whole blood cells or the treated PBMCs in the pharmaceutical composition is in the range of from 7.5×10$^6$ cells to 1.8×10$^{14}$ cells, preferably from 3.0×10$^7$ to 9.0×10$^{12}$ cells, particularly preferably from 6.0×10$^7$ to 7.5×10$^{11}$ cells
and/or
the concentration of the treated whole blood cells or the treated PBMCs in the pharmaceutical composition is in the range of from 10$^2$ cells to 10$^{10}$ cells/mL, preferably from 10$^6$ cells to 10$^9$ cells/mL.

A further aspect of the present invention relates to an ex vivo method for producing a pharmaceutical composition according to the invention, comprising the following steps:
a) obtaining a blood cell sample from the donor and optionally preparing Peripheral Blood Mononuclear Cells (PBMCs) from said blood cell sample,
b) treating the cells obtained in step a) ex vivo with a therapeutically effective amount of an active substance,
c) optionally: providing a pharmaceutically acceptable carrier and adding the carrier to the treated cells obtained in step b).

First, the obtained cells are carefully washed with a washing buffer. Then, a buffer is added to the reconstituted active agent(s) in a proportion of about 4:1. Thereafter, the mixture of buffer and active agent(s) is added to the cells (10$^6$-10$^9$ cells/ml) to obtain a concentration of 10-105 µg/ml. After an incubation time of 30 min at 37° C., the cells are centrifuged carefully. Afterwards, the cells are extensively washed to remove the active agent(s). For the quality control, the final product is tested for cell count, viability and composition of cells by flow cytometry, for sterility by the direct inoculation method according to Ph. Eur. 2.6.1, for freedom of endotoxins by the limulus amoebocyte lysate test according to Pharm Eur 2.6.14 and for quantification of the washed-out active agent(s) by high performance liquid chromatography. Additionally, according to the respective guidelines, infectious disease markers are tested from donor blood samples.

Everything that was said herein with regard to the pharmaceutical composition for use, for the pharmaceutical composition independent of its use as well as for the components of such a composition preferably also applies for a pharmaceutical composition as produced by the method as described herein.

It is preferred that in the pharmaceutical composition produced by the method as described herein, the total amount of the treated whole blood cells or the treated PBMCs is in the range of from $7.5 \times 10^6$ cells to $1.8 \times 10^{14}$ cells, preferably from $3.0 \times 10^7$ to $9.0 \times 10^{12}$ cells, particularly preferably from $6.0 \times 10^7$ to $7.5 \times 10^{11}$ cells and/or in the range of from $10^2$ cells to $10^{10}$ cells/mL, preferably from $10^6$ cells to $10^9$ cells/mL.

It is further preferred that in the pharmaceutical composition produced by the method as described herein, the concentration of the treated whole blood cells or the treated PBMCs is in the range of from $10^2$ cells to $10^{10}$ cells/mL, preferably from $10^6$ cells to $10^9$ cells/mL.

Compared to what is described above, also in the pharmaceutical composition produced by the method as described herein it is preferred that the active substance comprises or consists of one or more substances selected from the group consisting of chemotherapeutics, proteasome inhibitors, immunosuppressive agents, anti-proliferative substances and combinations thereof, preferably that the active substance comprises or consists of one or more substances selected from the group consisting of mitomycin C, C2 ceramide, tunicamycin, mycophenolate-mofetil, tryptophan metabolites and semisynthetic derivatives thereof, particularly preferably that the active substance comprises or consists of mitomycin C.

Moreover, in the pharmaceutical composition produced by the method as described herein it is preferred that the pharmaceutically acceptable carrier is present and comprises or consists of one or more substances selected from the group consisting of sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil, safflower oil, sesame oil, olive oil, corn oil and soybean oil; glycols, such as propylene glycol; esters such as ethyl oleate and ethyl laurate; agar; buffering agents such as magnesium hydroxide and aluminium hydroxide; alginic acid; pyrogen-free water; isotonic saline; Ringer's solution; ethyl alcohol, phosphate buffer solutions; non-toxic, compatible lubricants such as sodium lauryl sulfate and magnesium stearate; as well as colouring agents, releasing agents, coating agents, sweetening, flavouring and perfuming agents, preservatives and antioxidants.

Figure 1:
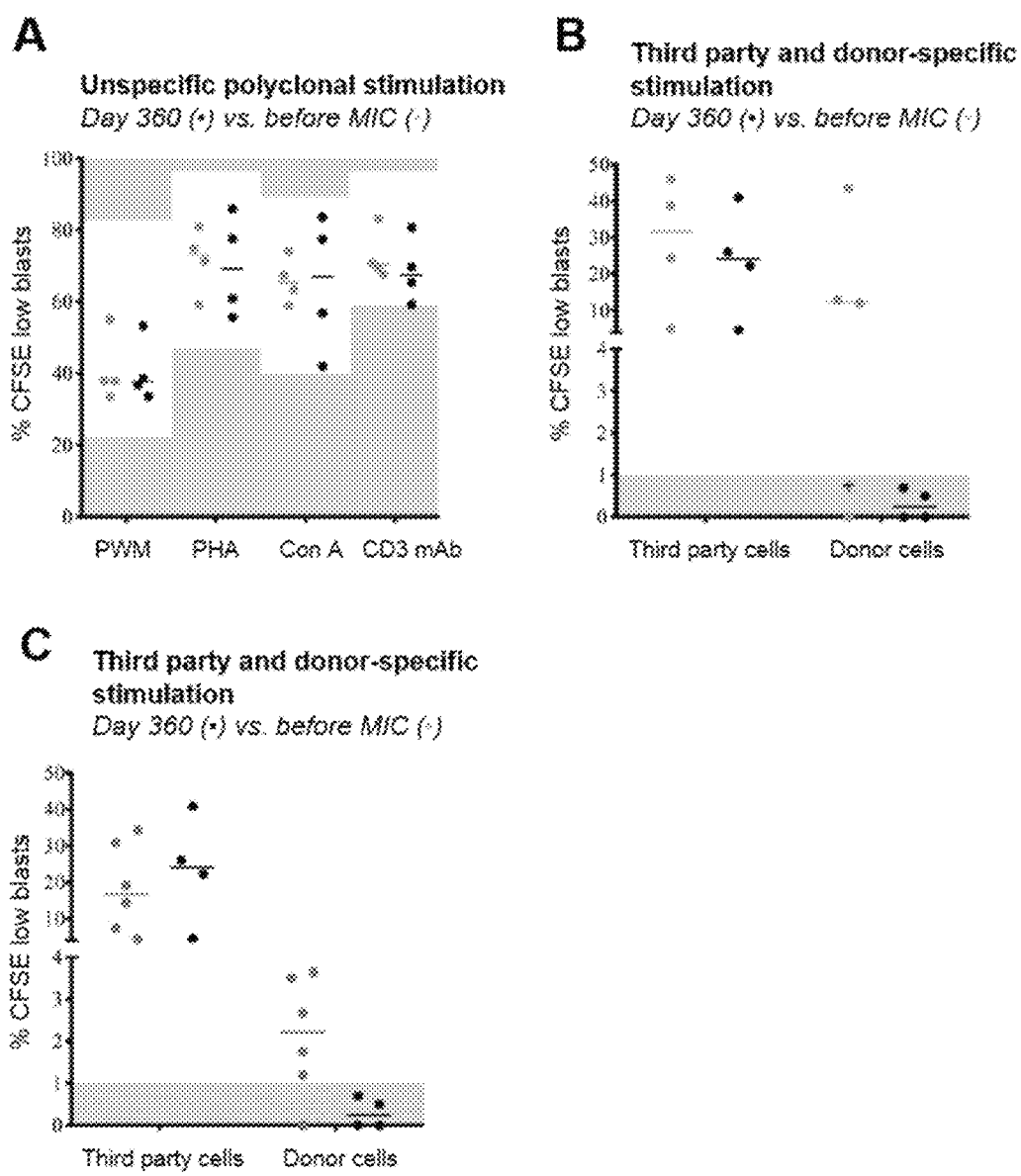
FIG. 1 describes the maintenance of an intact general immune system, wherein an unspecific polyclonal stimulation (FIG. 1A) or a third party, or a donor-specific stimulation (FIGS. 1B and C) was performed. The third party and donor-specific stimulation was compared to patients before the treatment (FIG. 1B) or to untreated controls (FIG. 1C).

Also described herein is a method for preventing or treating organ graft rejection or graft-versus-host disease in a human graft recipient, said method comprising the following steps:
  a) obtaining a blood cell sample from the donor, preferably from the graft donor, and optionally preparing Peripheral Blood Mononuclear Cells (PBMCs) from said blood cell sample,
  b) treating said blood cell sample or PBMCs derived therefrom with a therapeutically effective amount of an active substance, and
  c) administering the treated blood cell sample or PBMCs derived therefrom to the graft recipient and thereby treating an organ or cell graft rejection, wherein the amount of the cells of the administered treated blood cell sample or PBMCs derived therefrom is at least $0.25 \times 10^6$ cells per kg body weight, preferably at least $1.5 \times 10^6$ cells per kg body weight of the recipient.

All the features described with regard to the pharmaceutical composition and/or the pharmaceutical composition for use also apply for the method described herein, where applicable.

For this method it is preferred that the treated blood cells or PBMCs administered to the recipient comprise or consist of lymphocytes, monocytes and/or dendritic cells.

Further preferred in this method is that the chemotherapeutic agent is selected from the group consisting of mitomycin C, C2 ceramide, tunicamycin, mycophenolate-mofetil, tryptophan metabolites and semisynthetic derivatives thereof, and proteasome inhibitors.

It is also preferred in the method that the active substance comprises or consists of tryptophan metabolites (such as kynurenines, e.g. Tranilast) and/or mitomycin C.

Preferably in this method, the amount of the cells of the administered treated blood cell sample or PBMCs derived therefrom is at least $5 \times 10^6$ cells, at least $1 \times 10^7$ cells, at least $5 \times 10^7$ cells, at least $1 \times 10^8$ cells or at least $1.5 \times 10^8$ cells per kg body weight of the recipient.

Further preferred for this method is that the treated blood cell sample or PBMCs derived therefrom is/are administered to the recipient at least 1 day before the transplantation, at least 2 days, at least 3 days, at least 4 days, at least 5 days, at least 6 days, at least 7 days, at least 8 days, at least 9 days, at least 10 days, at least 14 days, at least 21 days or at least 28 days before the transplantation.

The skilled person will be well aware of the fact that the specific combination of cell number and time of application may depend on several individual factors of the subject such as the severity of the disorder, the age, body weight, general health, sex and diet of the patient, route of administration, the duration of the treatment as well as drugs used in combination or coincidental with the treatment or may depend on the organ to be transplanted.

Preferably in this method, the administration of the treated blood cell sample or PBMCs derived therefrom is performed as intravenous injection, preferably as infusion.

Also described herein is a further aspect relating to a method for treating or preventing organ graft rejection in a human graft recipient, wherein the method comprises administering to the recipient a composition comprising:
a) isolated blood cells or Peripheral Blood Mononuclear Cells (PBMCs) treated with a therapeutically effective amount of an active substance, and
b) optionally a pharmaceutically acceptable carrier, wherein the amount of the treated blood cells or PBMCs in the composition is selected such that at least $0.25 \times 10^6$ cells, preferably at least $1.5 \times 10^6$ cells of the treated blood cells or PBMCs per kg body weight of the recipient are administered.

Preferably, the method may also be suitable for treating and/or preventing of graft versus host disease.

All the features described with regard to the pharmaceutical composition and/or the pharmaceutical composition for use also apply for the method described herein, where applicable.

In this method it is preferred that the treated blood cells or PBMCs administered to the recipient comprise lymphocytes, monocytes and/or dendritic cells.

It is particularly preferred that the active substance comprises or consists of one or more substances selected from the group consisting of mitomycin C, C2 ceramide, tunicamycin, mycophenolate-mofetil, tryptophan metabolites (such as kynurenines, e.g. Tranilast) and semisynthetic derivatives thereof.

It is also preferred in the method that the active substance comprises or consists of tryptophan metabolites (such as kynurenines, e.g. Tranilast) and/or mitomycin C.

Preferably in this method, the amount of the cells of the administered treated blood cell sample or PBMCs derived therefrom is at least $5 \times 10^6$ cells, at least $1 \times 10^7$ cells, at least $5 \times 10^7$ cells, at least $1 \times 10^8$ cells or at least $1.5 \times 10^8$ cells per kg body weight of the recipient.

Further preferred for this method is that the treated blood cell sample or PBMCs derived therefrom is/are administered to the recipient at least 1 day before the transplantation, at least 2 days, at least 3 days, at least 4 days, at least 5 days, at least 6 days, at least 7 days, at least 8 days, at least 9 days, at least 10 days, at least 14 days, at least 21 days or at least 28 days before the transplantation.

The skilled person will be well aware of the fact that the specific combination of cell number and time of application may depend on several individual factors of the subject such as the severity of the disorder, the age, body weight, general health, sex and diet of the patient, route of administration, the duration of the treatment as well as drugs used in combination or coincidental with the treatment or may depend on the organ to be transplanted.

Preferably in this method, the administration of the treated blood cell sample or PBMCs derived therefrom is performed as intravenous injection, preferably as infusion.

Preferred embodiments and further aspects of the present invention emerge from the attached claims and the following examples, the examples not being intended to limit the invention.

EXAMPLES

Example 1

TOL-1 Study

A 30-day single-arm, single-centre phase I clinical trial for the determination of safety and feasibility of the intravenous administration of MICs for individualized immunosuppression was carried out in living donor kidney transplant recipients (TOL-1 Study, Ethics number: AFmo-549/2014, EudraCT number: 2014-002086-30, ClinicalTrials.gov Identifier: NCT02560220) followed by an observational phase up to day 360 after transplantation (Ethics numbers: 082/2005, 083/2005, S-395/2011). The study was performed in compliance with the provisions of the Declaration of Helsinki and the Good Clinical Practice Guidelines.

Primary outcome measure was the safety and feasibility of intravenous administration of MICs as measured by the frequency of adverse events (AEs) in patients with chronic kidney disease stage 4 or 5 (i.e. GFR <30 mL/min) who received a kidney transplant from a living donor. AEs were recorded according to Common Terminology Criteria for Adverse Events (CTCAE), version 4.03.

From August 2015 to February 2017, 14 donor and recipient pairs were screened for inclusion into the study. A total of 12 donors received leukapheresis and finally 10 patients were treated with the MIC product. The observation phase was for an additional 330 days up to February 2018.

10 patients (groups A, B, C) received MICs from their donor prior to kidney transplantation. Patients received either $1.5 \times 10^6$ MICs per kg body weight on day −2 (N=3, group A) or $1.5 \times 10^8$ MICs per kg body weight on day −2 (N=3, group B) or day −7 (N=4, group C) prior to living donor kidney transplantation.

Baseline characteristics of patients are given in Table 1.

TABLE 1

Baseline patient characteristics

| | Screened (N = 14) | Total treated (N = 10) | Group A (N = 3) | Group B (N = 3) | Group C (N = 4) |
|---|---|---|---|---|---|
| Patient | | | | | |
| Age (years) - median (range) | 45 (22-59) | 40 (22-59) | 36 (34-47) | 28 (22-59) | 46 (29-50) |
| Male sex - N (%) | 11 (79) | 8 (80) | 3 (100) | 2 (67) | 3 (75) |

TABLE 1-continued

| Baseline patient characteristics | | | | | |
|---|---|---|---|---|---|
| | Screened (N = 14) | Total treated (N = 10) | Group A (N = 3) | Group B (N = 3) | Group C (N = 4) |
| Cause of ESRD - N (%) | | | | | |
| Vascular | 0 (0) | 0 (0) | 0 (0) | 0 (0) | 0 (0) |
| Diabetes mellitus | 0 (0) | 0 (0) | 0 (0) | 0 (0) | 0 (0) |
| Glomerulonephritis | 8 (57) | 5 (50) | 2 (67) | 1 (33) | 2 (50) |
| Polycystic kidney disease | 2 (14) | 2 (20) | 0 (0) | 1 (33) | 1 (25) |
| Other | 4 (29) | 3 (30) | 1 (33) | 1 (33) | 1 (25) |
| Living donor | | | | | |
| Living related - N (%) | 10 (71) | 8 (80) | 2 (67) | 2 (67) | 4 (100) |
| Age (years) - median (range) | 54 (42-68) | 54 (42-61) | 51 (46-58) | 54 (47-61) | 55 (42-57) |
| Male sex - N (%) | 4 (29) | 3 (30) | 0 (0) | 1 (33) | 2 (50) |
| Serological data | | | | | |
| CMV serologic status - N (%) | | | | | |
| Donor negative, recipient negative | 5 (36) | 3 (30) | 1 (33) | 1 (33) | 1 (25) |
| Donor negative, recipient positive | 1 (7) | 0 (0) | 0 (0) | 0 (0) | 0 (0) |
| Donor positive, recipient positive | 5 (36) | 5 (50) | 1 (33) | 2 (67) | 2 (50) |
| Donor positive, recipient negative | 3 (21) | 2 (20) | 1 (33) | 0 (0) | 1 (25) |
| EBV virus serologic status - N (%) | | | | | |
| Donor negative, recipient negative | 0 (0) | 0 (0) | 0 (0) | 0 (0) | 0 (0) |
| Donor negative, recipient positive | 1 (7) | 0 (0) | 0 (0) | 0 (0) | 0 (0) |
| Donor positive, recipient positive | 12 (86) | 10 (100) | 3 (100) | 3 (100) | 4 (100) |
| Donor positive, recipient negative | 1 (7) | 0 (0) | 0 (0) | 0 (0) | 0 (0) |
| Immunological data | | | | | |
| HLA A-, B-, DR-mismatches - N (%) | | | | | |
| 0 | 2 (14) | 2 (20) | 1 (33) | 0 (0) | 1 (25) |
| 1 | 1 (7) | 1 (10) | 0 (0) | 0 (0) | 1 (25) |
| 2 | 1 (7) | 1 (10) | 0 (0) | 0 (0) | 1 (25) |
| 3 | 6 (43) | 4 (40) | 1 (33) | 2 (67) | 1 (25) |
| 4 | 0 (0) | 0 (0) | 0 (0) | 0 (0) | 0 (0) |
| 5 | 4 (29) | 2 (20) | 1 (33) | 1 (33) | 0 (0) |
| 6 | 0 (0) | 0 (0) | 0 (0) | 0 (0) | 0 (0) |
| Patients with sensitizing events - N (%) | | | | | |
| Transplantation | 0 (0) | 0 (0) | 0 (0) | 0 (0) | 0 (0) |
| Blood transfusion | 3 (21) | 2 (20) | 0 (0) | 0 (0) | 2 (50) |
| Pregnancy | 0 (0) | 0 (0) | 0 (0) | 0 (0) | 0 (0) |
| PRA (%) - median (range) | | | | | |
| T cell (−DTT) | 0 (0-6) | 0 (0-6) | 0 (0-0) | 0 (0-1) | 2 (0-6) |
| T cell (+DTT) | 0 (0-4) | 0 (0-4) | 0 (0-0) | 0 (0-0) | 2 (0-4) |
| B cell (−DTT) | 0 (0-12) | 0 (0-12) | 0 (0-0) | 0 (0-12) | 0 (0-4) |
| B cell (+DTT) | 0 (0-35) | 2 (0-35) | 4 (0-12) | 0 (0-35) | 2 (0-4) |
| Luminex (HLA class I) | 0 (0-2) | 0 (0-2) | 0 (0-0) | 1 (0-2) | 0 (0-2) |
| Luminex (HLA class II) | 0 (0-9) | 1 (0-9) | 0 (0-1) | 0 (0-2) | 3 (0-9) |
| Patients with pretransplant DSA - N (%) | 0 (0) | 0 (0) | 0 (0) | 0 (0) | 0 (0) |

CMV = cytomegalovirus,
DSA = donor-specific HLA A-, B-, DR-, DQ-antibodies,
DTT = dithiothreitol,
EBV = Epstein-Barr virus,
ESRD = end-stage renal disease,
HLA = human leukocyte antigen,
PRA = panel-reactive antibody Four patients (R8, R9, R10, R13) were screened but received no cell therapy.

All other patients (N=10: R1, R2, R3, R4, R5, R6, R7, R11, R12, R14) as well as the corresponding donors were treated per protocol (as described above).

Unstimulated donor leukapheresis was performed with a Spectra Optia® apheresis device (Terumo BCT, Eschborn, Germany). MICs were produced under Good Manufacturing Practice (GMP) conditions. The MIC product was administered to the patients at the same day of donor leukapheresis and product preparation as a one-time administration. Patients of group A had a prescribed dose of $1.5 \times 10^6$ MICs per kg b.w. 2 days before transplantation. Patients of group B had a prescribed dose of $1.5 \times 10^8$ MICs per kg b.w. 2 days before transplantation. In patients of group C, MICs were administered at a prescribed dose of $1.5 \times 10^8$ MICs per kg b.w. already 7 days prior to transplantation. The patients were assigned to the groups A (R1-R3), B (R4-R6) or C (R7, R11, R12, R14) and received the MICs. The actual administered MIC doses are given in Table 2.

TABLE 2

Unstimulated leukapheresis in 12 donors

| | | | Clinical parameter | | | GMP | | | Quality control of MIC end-product | | |
|---|---|---|---|---|---|---|---|---|---|---|---|
| | Production | | Blood | Blood | Achieved | MIC | Absolut nuclear cell | CD14+ | | Endotoxin | Mitomycin C |
| Group | Donor no. | Recipient no. | group donor | group recipient | cell dose per kg b.w. | end-product volume (mL) | amount ×10⁸ (Neubauer) | cells (%) | Sterility (Ph.Eur.) | (EU/mL, Ph.Eur.) | (µg/mL, Ph.Eur.) |
| A | D1 | R1 | A Rh. pos. | A Rh. pos. | $1.5 \times 10^6$ | 85.1 | 1.3 | 11.7 | sterile | 0.79 | <LOD |
| A | D2 | R2 | A Rh. pos. | A Rh. pos. | $1.5 \times 10^6$ | 80.7 | 1.2 | 10.4 | sterile | 1.38 | 0.1 |
| A | D3 | R3 | O Rh. pos. | O Rh. pos. | $1.5 \times 10^6$ | 79.1 | 1.2 | 19.2 | sterile | 1.56 | 0.0 |
| B | D4 | R4 | A Rh. pos. | A Rh. pos. | $1.5 \times 10^8$ | 93.8 | 105.0 | 23.2 | sterile | 0.72 | 0.0 |
| B | D5 | R5 | O Rh. pos. | O Rh. pos. | $1.5 \times 10^8$ | 85.0 | 87.0 | 17.2 | sterile | 1.72 | 0.0 |
| B | D6 | R6 | O Rh. pos. | O Rh. pos. | $0.4 \times 10^{8}$* | 91.6 | 43.0 | 16.2 | sterile | 1.31 | 0.0 |
| C | D7 | R7 | O Rh. neg. | O Rh. neg. | $1.5 \times 10^8$ | 64.3 | 134.0 | 16.4 | sterile | 1.08 | 0.0 |
| C | D11 | R11 | O Rh. neg. | A Rh. neg. | $1.5 \times 10^8$ | 91.8 | 96.0 | 15.9 | sterile | 1.97 | 0.5 |
| C | D12 | R12 | O Rh. pos. | O Rh. pos. | $1.3 \times 10^{8}$# | 96.7 | 126.0 | 17.3 | sterile | 1.39 | 0.3 |
| C | D14 | R14 | O Rh. pos. | A Rh. pos. | $1.5 \times 10^8$ | 95.7 | 124.5 | 9.9 | sterile | 1.23 | 0.2 |

*In donor D6, only 60% of the targeted blood volume was processed during leukapheresis due to venous access problems and therefore patient R6 (male, 101 kg b.w) received a reduced dose of only $0.4 \times 10^8$ MICs per kg b.w,.
In donor D12. leukapheresis was performed per protocol but the cells obtained were only sufficient for a cell dose of $1.3 \times 10^8$ MICs per kg b.w. in patient R12 (male, 105 kg b.w.).
b.w. = body weight,
CD = cluster of differentiation,
EU = endotoxin units,
GMP = Good Manufacturing Practice,
LOD = limit of detection,
MIC = modified immune cells,
n.a. = not applicable,
pat. = patient,
Ph.Eur. = Pharmacopoea Europaea Patients were treated in a stepwise approach with a dose escalation from group A to group B to account for possible adverse reactions to the MIC end product such as embolism, inflammation, allergy or an adverse reaction to mitomycin C or the buffer. Since a too small MIC cell number confers the risk of recipient sensitization (recipients of group A had only 1% of the MIC cell number of patients of groups B and C), MICs were administered at least 2 days before transplantation during the dose escalation phase. From group B to group C, the administration time point was changed from day −2 to day −7 before transplantation.

During recipient visit V3 on day −1 before transplant surgery, recipient sensitization by the MIC product was excluded by CDC and ELISA crossmatch and HLA antibody screening by the Luminex technique.

Post-transplant recipient visits were on day 7±1 (V4) and day 30±4 (V5, end of study). The observation phase was up to day 360 after kidney transplantation with frequent outpatient visits on days 60±14, 90±14, 135±21, 180±21, 225±28, 270±28, 360±35.

Figure 2C:
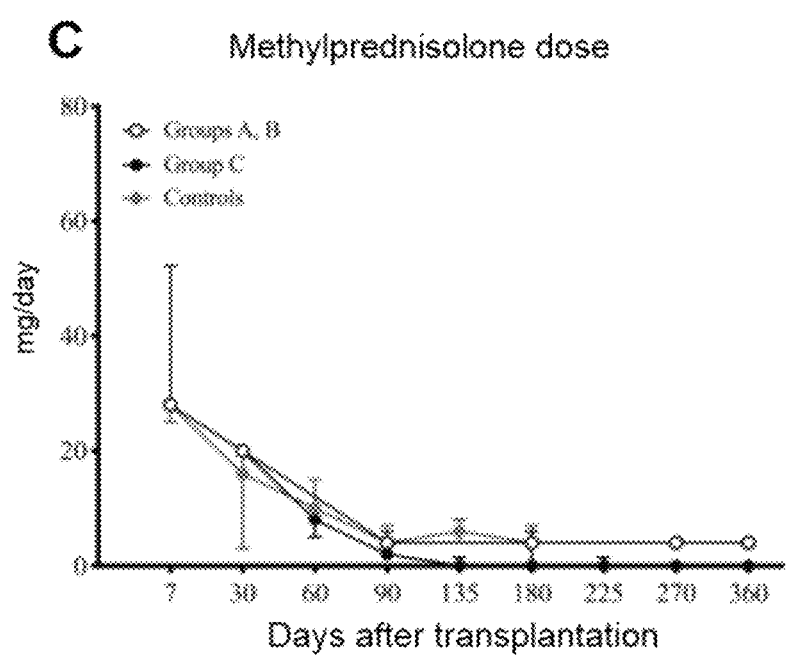
FIG. 2 describes the immunosuppression, i.e. the Cyclosporine A trough level (A), the daily enteric-coated mycophenolic sodium dose (EC-MPS) (B) and the daily methylprednisolone dose (C), in patients of groups A, B, C and controls.

Immunosuppression consisted of cyclosporin A (CyA), enteric-coated mycophenolic sodium (EC-MPS) and methylprednisolone (MPS) given from the day of surgery. In patients of group C, immunosuppressive therapy was reduced to low dose CyA and low dose EC-MPS without steroids during the observation phase beyond day 30 to avoid infectious complications of a combined cell-based and immunosuppressive therapy. Patients of groups A and B received immunosuppression according to the standard of care. These standards are known to the skilled person. The immunosuppression applied to patients of the control group was selected such that it resulted in an immunosuppression comparable to the one obtained in patients of group C. The detailed immunosuppressive therapy in patients during the TOL-1 study and observation phase is given in FIG. 2A-C.

Data collected during the first 30 days after transplantation showed that MIC infusions were excellently tolerated. A total of 69 adverse events (AEs) including 3 severe AEs (SAEs) occurred in the 10 treated patients. AEs were either unlikely related (N=1) or unrelated (N=68) to MIC therapy. During the study phase, no positive crossmatch results, de novo donor specific antibodies, or rejection episodes occurred with excellent kidney graft function in all patients (cf. FIG. 3A-C and Table 2).

Example 1.1

No Detectable Donor Chimerism After MIC Infusion

Already one day after MIC infusion, no donor chimerism was detectable in the 10 patients. Absence of donor chimerism was confirmed on day −1 before, and on days 7 and 30 after transplantation.

Example 1.2

Excellent Clinical Outcomes Up to One Year After Transplantation

Figure 3C:
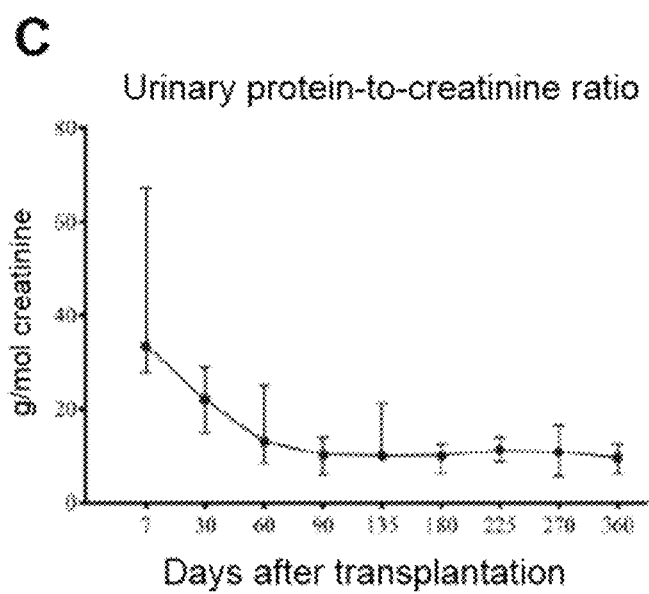
FIG. 3 describes the achieved and maintained organ (kidney) function, analysed by the levels of serum creatinine (FIG. 3A), by the glomerular filtration rate (GFR, calculated according to the Chronic Kidney Disease Epidemiology Collaboration (CKD-EPI) formula) (FIG. 3B) or the urinary protein-to-creatinine ratio (FIG. 3C).

During the observation phase, no de novo donor specific antibodies, or rejection episodes occurred and all patients had an excellent kidney graft function (cf. FIG. 3A-C and Table 3). On day 360 after surgery, the median serum creatinine was 1.4 mg/dL (1.1-2.1), median eGFR 58 mL/min (37-75) and median urinary protein excretion 10 g/moL creatinine (3-19). No opportunistic infections were recorded. A total of 10 non-opportunistic infectious episodes occurred in 4 out of 10 patients. This included 3 episodes of urinary tract infection in patient R7 who suffered from a small-capacity urinary bladder, and 2 episodes of urinary tract infection in patient R12. No new-onset diabetes (NO-DAT), leukopenia, diarrhea episode, post-transplant lymphoproliferative disease (PTLD) or other malignancies were observed. The total anti-hypertensive therapeutic intensity score was lower on day 360 after transplantation as compared to before surgery, particularly in patients of group C, while normal blood pressure was maintained.

All patients showed excellent kidney graft function with no proteinuria up to day 360 after surgery (cf. FIG. 3C).

absent tubulitis (t1) indicative for allergic interstitial nephritis. Methylprednisolone was given at 125 mg per 3 days and serum creatinine returned to baseline in both patients.

Therefore, it was followed that also the biopsies revealed that no allograft rejection occurred.

TABLE 3

Outcomes and complications in 10 patients (TOL-1 study phase and observation phase up to day 360)

|  | Total treated (N = 10) | Group A (N = 3) | Group B (N = 3) | Group C (N = 4) |
|---|---|---|---|---|
| Biopsy-proven rejection (≥BANFF IA) - N (%) | 0 (0) | 0 (0) | 0 (0) | 0 (0) |
| Development of de novo DSA (A, B, DR, DQ) at a cut-off of >1,000 MFI - N (%) | 0 (0) | 0 (0) | 0 (0) | 0 (0) |
| Patients with opportunistic infections - N (%) | 0 (0) | 0 (0) | 0 (0) | 0 (0) |
| Infectious episodes - N | 0 | 0 | 0 | 0 |
| Pneumonia | 0 | 0 | 0 | 0 |
| CMV reactivation >1,000 copies/mL | 0 | 0 | 0 | 0 |
| BKV replication >1,000 copies/mL | 0 | 0 | 0 | 0 |
| BKV-associated nephropathy | 0 | 0 | 0 | 0 |
| Other infection | 0 | 0 | 0 | 0 |
| Patients with non-opportunistic infections - N (%) | 4 (40) | 1 (33) | 0 (0) | 3 (75) |
| Infectious episodes - N | 10 | 1 | 0 | 9 |
| CV-associated infection | 1 | 1 | 0 | 0 |
| Urinary tract infection | 6 | 0 | 0 | 6 |
| Post-operative wound infection | 1 | 0 | 0 | 1 |
| Pneumonia | 1 | 0 | 0 | 1 |
| Other infection | 1 | 0 | 0 | 1 |
| PTLD or malignancy - N (%) | 0 (0) | 0 (0) | 0 (0) | 0 (0) |
| Blood pressure on day 360 - median (range) |  |  |  |  |
| Systolic blood pressure (mmHg) | 125 (110-145) | 130 (110-145) | 120 (120-130) | 129 (120-140) |
| Total anti-hypertensive TIS | 0.75 (0.13-2.5) | 0.75 (0.5-1.5) | 1.5 (0.13-1.5) | 0.75 (0.17-2.5) |
| Change of total anti-hypertensive TIS from baseline | −0.22 (−4.63-0.75) | −0.25 (−2.25-0) | 0 (−0.19-0.75) | −1.04 (−4.63-0) |
| NODAT - N (%) | 0 (0) | 0 (0) | 0 (0) | 0 (0) |
| Leukopenia <3.5/nL - N (%) | 0 (0) | 0 (0) | 0 (0) | 0 (0) |
| Documented diarrhea - N (%) | 0 (0) | 0 (0) | 0 (0) | 0 (0) |
| Patients with surgical complications* - N (%) | 4 (40) | 0 (0) | 2 (67) | 2 (50) |
| Bleeding | 1 (10) | 0 (0) | 0 (0) | 1 (25) |
| Wound healing disturbances | 2 (20) | 0 (0) | 2 (67) | 0 (0) |
| Urinary leakage | 1 (10) | 0 (0) | 0 (0) | 1 (25) |
| Lymphocele | 0 (0) | 0 (0) | 0 (0) | 0 (0) |

*requiring intervention.
BKV = BK virus,
CMV = cytomegalovirus,
CV = central venous catheter,
DGF = delayed graft function,
DSA = donor-specific antibody,
MFI = mean fluorescence intensity,
NODAT = new-onset diabetes after transplantation,
PTLD = post-transplant lymphoproliferative disease,
TIS = therapeutic intensity score Additionally, protocol biopsies on day 7 after transplantation showed no allograft rejection. Indication biopsies due to a transient rise in serum creatinine were performed in patients R2 and R14 but showed no abnormalities. In both patients, serum creatinine returned to baseline without further measures. Patient R1 from group A, who received only 1% of the MIC cell number administered to groups B and C, was found to have borderline changes in a biopsy on day 77. In this patient, the biopsy was performed after a rise in serum creatinine of 0.2 mg/dL from baseline. Patient R11 was found to have E. coli urinary tract infection on day 128 after surgery requiring a quinolone antibiotic. Serum creatinine rose from 1.31 mg/dL before antibiotic treatment to a maximum of 1.81 mg/dL on day 157. A biopsy procedure revealed severe interstitial inflammation (i3) with nearly Example 1.3

Anti-Donor T Lymphocyte Responses in MIC-Treated Patients

Patients from group C showed preserved lymphocyte proliferation in response to unspecific polyclonal stimulators on day 360 after transplantation as compared to before MIC infusion, indicating an intact general immune response (cf. FIG. 1A). This was confirmed by allogeneic stimulation with third party cells (cf. FIG. 1B). In contrast, the T-cell response against the donor was absent on day 360 as compared to before MIC infusion (cf. FIG. 1B). Whereas MIC-treated patients had suppressed T lymphocyte responses, 5 out of 6 control patients showed preserved reactivity to the donor (cf. FIG. 1C).

Example 1.4

HLA Antibodies and Antibody Titers to Bacterial and Viral Immunizations

During the observation phase no de novo donor-specific antibodies were detected. This finding raised the question whether the memory B cell response to donor-unrelated antigens as induced by previous immunizations was also affected. Titer for measles (median 4400 mIU/mL, 200-11, 000), mumps (median 400, 230-8000), rubella (median 41 IU/mL, 9-160), varicella (median 1350 mIU/mL, 410-3500), diphtheria (median 0.165 IU/mL, 0.04-0.33) and tetanus (median 1.45 IU/mL, 0.5-2.1) were lowest on day 30 after kidney transplantation, but reached pre-transplant levels during the further course.

Example 1.5

Pre-Transplant Levels of T Lymphocyte-, B Lymphocyte- and NK Cell Numbers One Year After Transplantation The number of $CD4^+$ and $CD8^+$ T lymphocytes as well as of activated $CD4^+$ and $CD8^+$ T lymphocytes remained stable before and after transplantation. $CD19^+$ B lymphocytes were highest on day 30 after surgery with a median of 300/μL (149-561) but returned to pre-transplant levels on day 180 with a median of 35/μL (25-247). $CD16^+CD56^+$ NK cells behaved inversely being lowest on day 30 post-transplant with a median of 60/μL (33-73) but increased to a median of 104 (93-154) on day 180.

Example 1.6

Unchanged Number of Regulatory T Lymphocytes But Strongly Increased Number of Regulatory B Lymphocytes Starting from Day 135 After Transplantation The regulatory T lymphocyte (Treg) number was low on day 30 after transplantation (cf. FIG. 4A-B) at the time of most powerful immunosuppressive therapy. The median percentage of $CD4^+CD25^+FoxP3^+CD127^-$ T lymphocytes then increased from 1% (0-1) to 3% (1-5) on day 180 (cf. FIG. 4B). This value was comparable to the pre-transplant and pre-treatment level of 2.5% (2-4).

Figure 4:
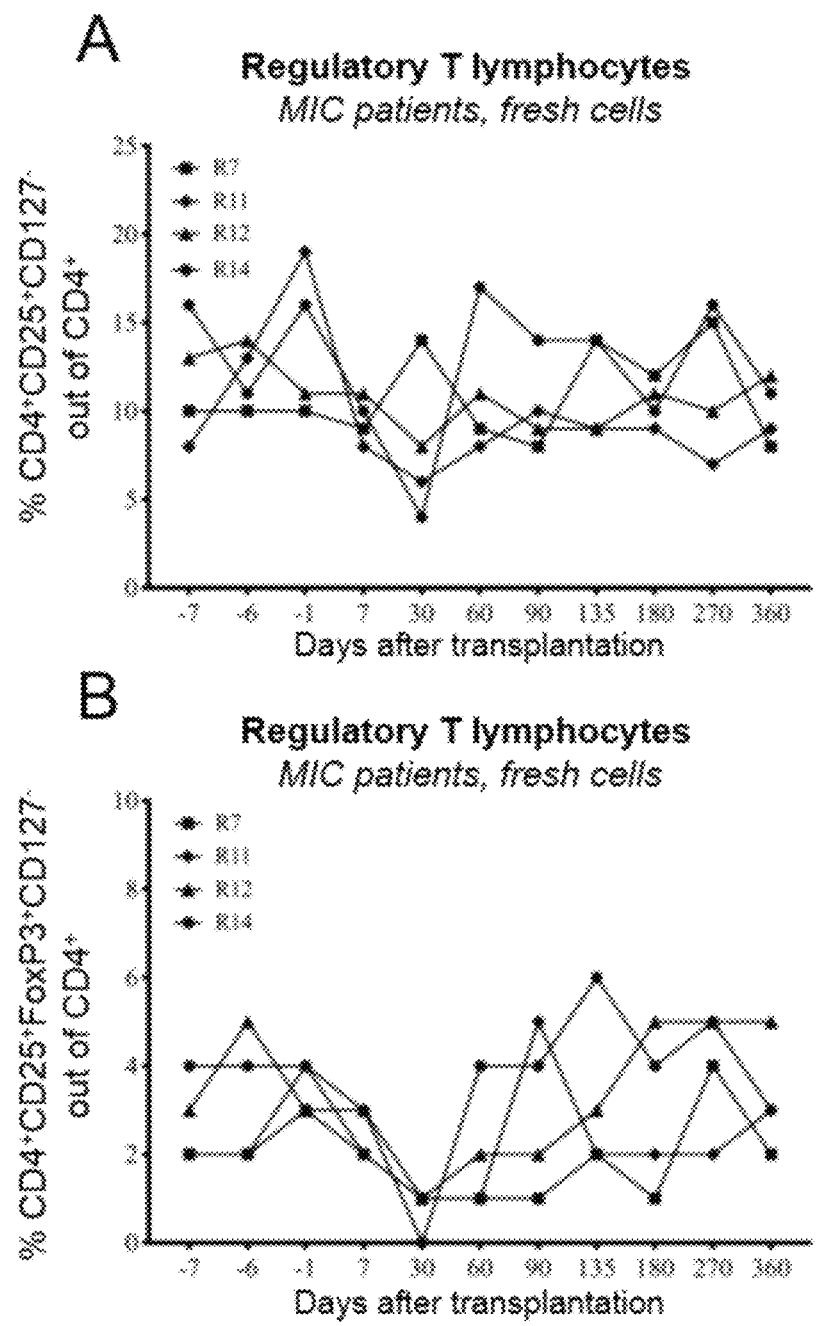
FIG. 4 describes the status of the regulatory T lymphocytes before and after the treatment, wherein $CD4^+CD25^+CD127^-$ (FIG. 4A) or $CD4^+CD25^+FoxP3^+CD127^-$ (FIG. 4B) T lymphocytes were analysed.
Figure 5:
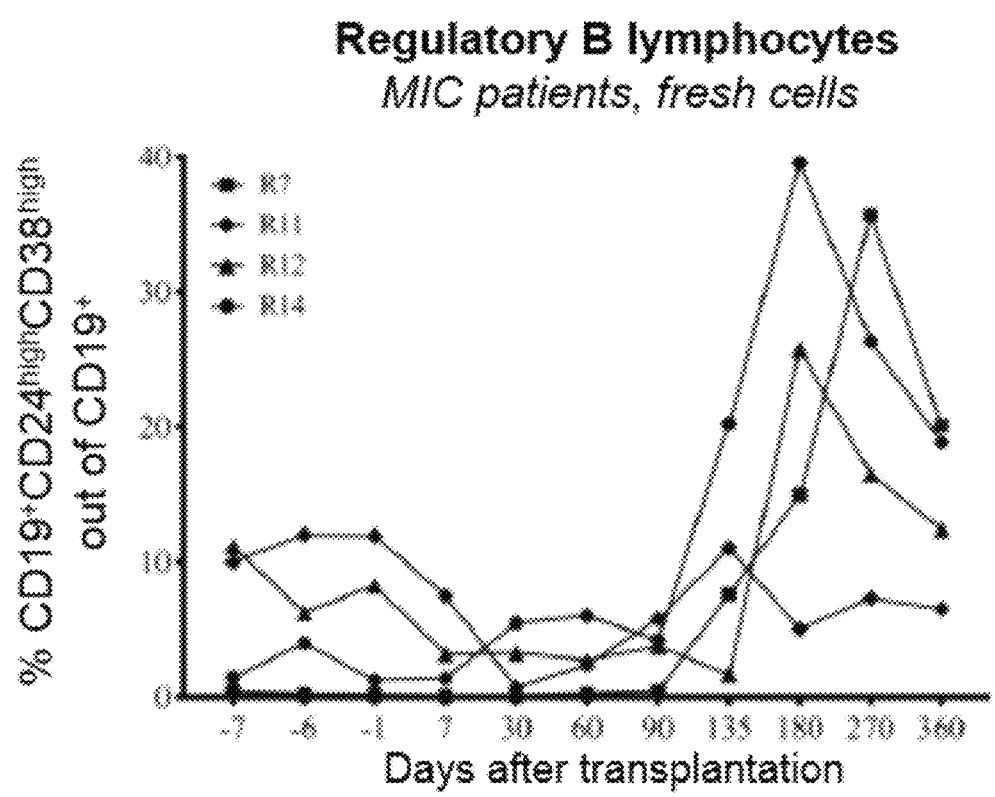
FIG. 5 describes the status of the regulatory B lymphocytes before and after the treatment within study group C, wherein $CD19^+CD24^{high}CD38^{high}$ regulatory B lymphocytes were analysed.

Interestingly, the percentage of $CD19^+CD24^{high}CD38^{high}$ immature B lymphocytes (regulatory B lymphocytes, Bregs) was low until day 90 after transplantation with a median of 2.0% (0.1-5.5) on day 30 (cf. FIGS. 4 and 5). Thereafter, Bregs increased to a median of 20.4% (5.0-39.6) on day 180, exceeding by far the pre-transplant levels which showed a median of only 5.7% (0.4-11.2) before MIC infusion. Only patient R11 with the need for systemic methylprednisolone therapy one month in advance showed a lower 5.0% of Bregs on day 180. In this patient, Bregs increased again reaching 17.0% at the last follow-up on day 670. Not only the relative proportion but also absolute Breg numbers increased from a median of 4.5/μL (0.3-14.8) on day 30 to 10/μL (3.8-15.3) on day 180 and 14.2 (4.0-23.9) on day 270.

Figure 7:
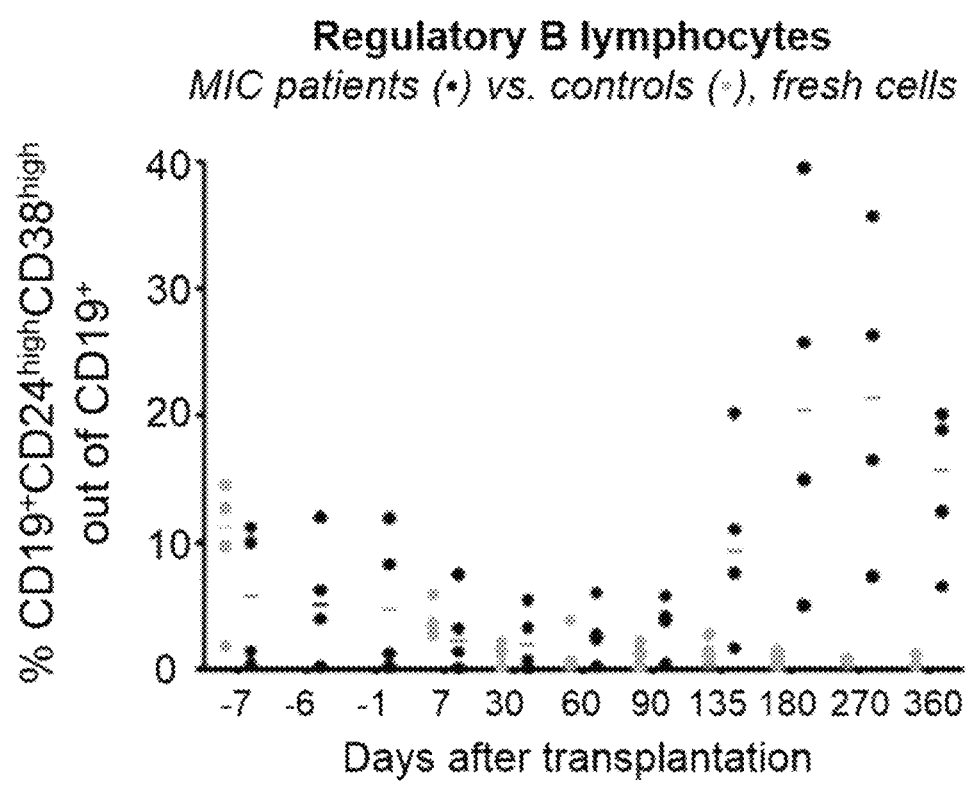
FIG. 7 describes the status of the regulatory B lymphocytes before and after the treatment, compared to untreated controls, wherein $CD19^+CD24^{high}CD38^{high}$ B lymphocytes were analysed.

Breg percentages in patients of group C in comparison to Breg percentages of 40 measurements in 31 matched kidney transplant recipients without MIC infusion are shown in FIG. 7. Before MIC infusion, the values were comparable between patients of group C and controls with a median of 5.7% versus 11.2%, respectively. In contrast, in MIC-treated patients Bregs dramatically increased post-transplant and were 19, 26 and 13 times higher 180, 270 and 360 days after transplantation, respectively, compared to controls.

Figure 6:
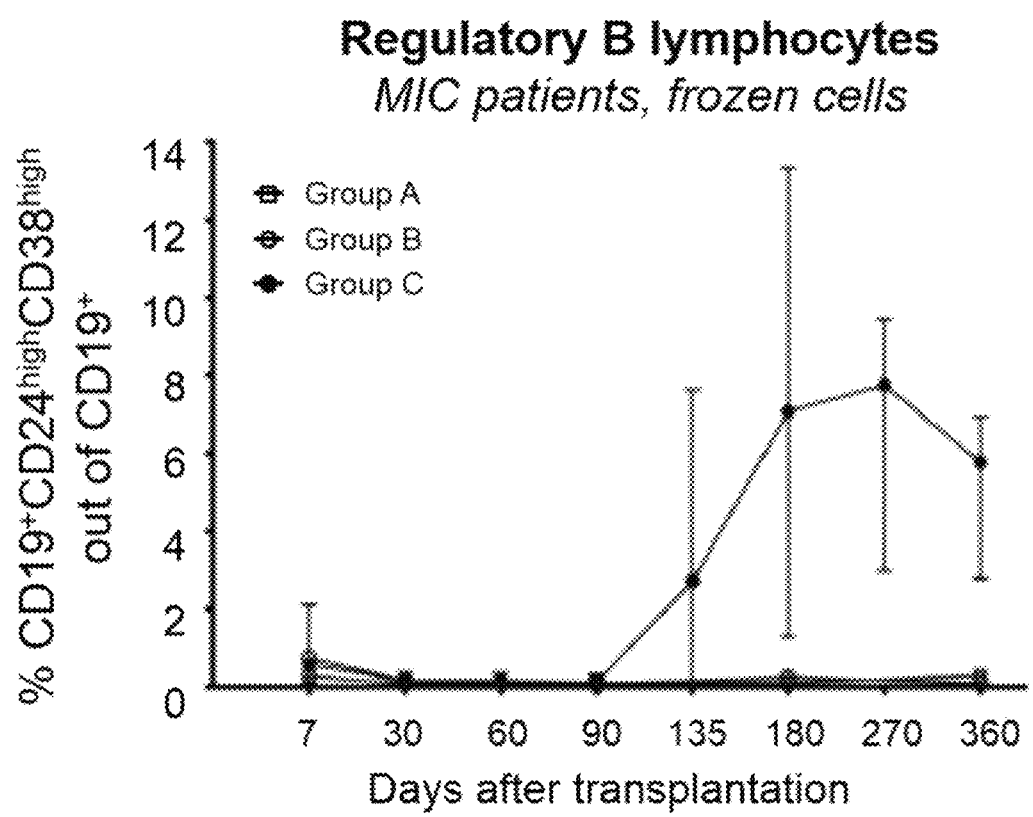
FIG. 6 describes the status of the regulatory B lymphocytes before and after the treatment of study groups A, B and C, wherein $CD19^+CD24^{high}CD38^{high}$ regulatory B lymphocytes were analysed.
Figure 8:
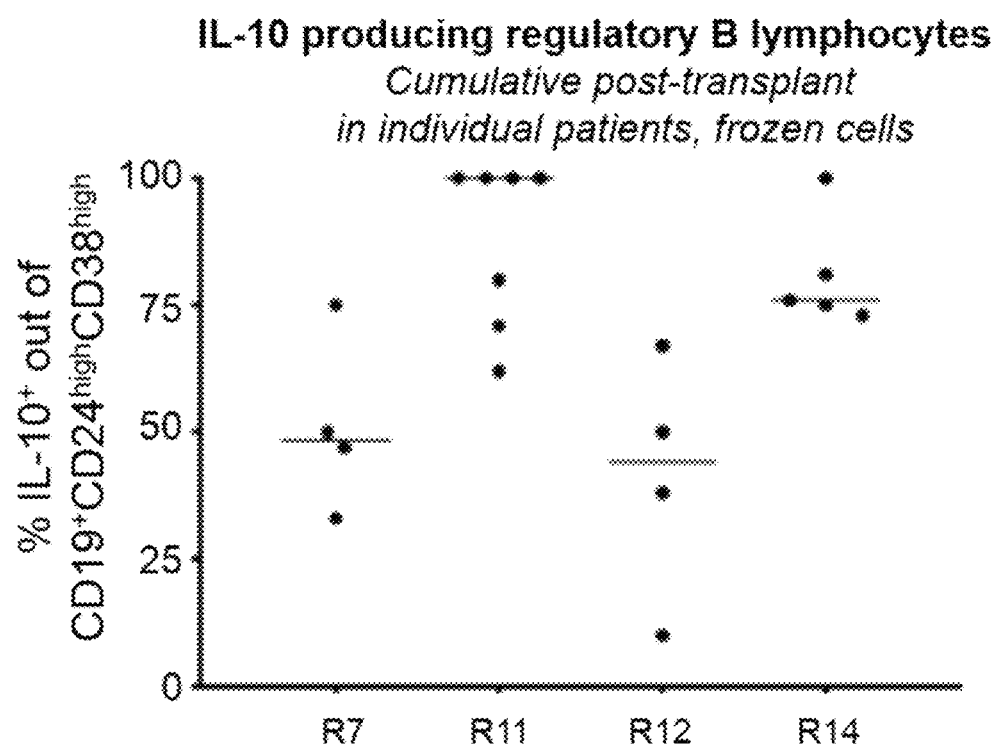
FIG. 8 describes the levels of $IL-10^+$ cells among the $CD19^+CD24^{high}CD38^{high}$ regulatory B lymphocytes of group C patients.

It was of particular interest, whether Bregs also increased in patients of groups A (receiving a reduced cell dose on day −2) and B (receiving the full cell dose on day −2). For this purpose, we analyzed Bregs from frozen samples. As expected, patients from group C showed the highest Breg percentages exceeding the values in patients of groups A and B by a factor of 68 and 20, respectively, on day 180 after transplantation (cf. FIG. 6). Most importantly, during the post-transplant course the majority of Bregs from patients of group C produced the immunosuppressive cytokine IL-10 (median of 44-100%) (cf. FIG. 8).

The invention claimed is:

1. A dosage of a pharmaceutical composition for a human graft recipient comprising:
   a) isolated whole blood cells and/or Peripheral Blood Mononuclear Cells (PBMCs) treated with a therapeutically effective amount of mitomycin C, wherein the isolated whole blood cells or PBMCs are obtained or derived from a human graft donor, and
   b) optionally a pharmaceutically acceptable carrier; wherein the dosage prevents or treats organ or cell graft rejection in the human graft recipient, and wherein the dosage comprises at least $1 \times 10^8$ cells of the treated whole blood cells and/or the treated PBMCs.

2. The dosage according to claim 1 comprising Peripheral Blood Mononuclear Cells (PBMCs), wherein the PBMCs comprise monocytes and lymphocytes.

3. The dosage according to claim 1 comprising the pharmaceutically acceptable carrier, wherein the pharmaceutically acceptable carrier is selected from of sugars; starches; cellulose and its derivates; powdered tragacanth; malt; gelatine; talc; cocoa butter; suppository waxes; oils; glycols; esters; agar; buffering agents; alginic acid; pyrogen-free water; isotonic saline; Ringer's solution; ethyl alcohol; phosphate buffer solutions; non-toxic, compatible lubricants; colouring agents; releasing agents; coating agents; sweetening, flavouring and perfuming agents; preservatives; and antioxidants.

4. A method for producing a dosage according to claim 1 comprising:
   a) obtaining a blood cell sample from the human graft donor and optionally preparing Peripheral Blood Mononuclear Cells (PBMCs) from said blood cell sample,
   b) treating the cells obtained in a) ex vivo with a therapeutically effective amount of mitomycin C, and
   c) optionally, providing a pharmaceutically acceptable carrier and adding the carrier to the treated cells obtained in b).

5. The method according to claim 4, wherein the total amount of the treated whole blood cells or the treated PBMCs in the dosage is at least $1.5 \times 10^8$ cells per kg body weight of the recipient.

6. The method according to claim 4, wherein the pharmaceutically acceptable carrier is present and selected from sugars; starches; cellulose and its derivatives; powdered tragacanth; malt; gelatine; talc; cocoa butter; suppository waxes; oils; glycols; agar; buffering agents; alginic acid; pyrogen-free water; isotonic saline; Ringer's solution; ethyl alcohol; phosphate buffer solutions; non-toxic, compatible lubricants; colouring agents; releasing agents; coating agents; sweetening, flavouring, and perfuming agents; preservatives; and antioxidants.

7. A method for preventing and/or treating organ and/or cell graft rejection in a human graft recipient comprising administering to the recipient an amount of a pharmaceutical composition comprising:
- a) isolated whole blood cells and/or Peripheral Blood Mononuclear Cells (PBMCs) treated with a therapeutically effective amount of mitomycin C,
  wherein the isolated whole blood cells or PBMCs are obtained or derived from a human graft donor; and
- b) optionally a pharmaceutically acceptable carrier;
  wherein the amount of the pharmaceutical composition administered to the recipient comprises at least $1 \times 10^8$ cells of the treated whole blood cells and/or the treated PBMCs per kg body weight of the recipient;
  wherein the pharmaceutical composition is administered to the recipient at least five days before an organ and/or cell transplantation.

8. The method according to claim 7, comprising administering to the recipient at least $1.5 \times 10^8$ cells of the treated whole blood cells or the treated PBMCs per kg body weight of the recipient.

9. The method according to claim 7, wherein the administration is performed as an intravenous, intramuscular, or subcutaneous injection, or as an infusion.

10. The method according to claim 7 comprising administering to the recipient at least $1.5 \times 10^8$ cells of the treated whole blood cells or the treated PBMCs per kg body weight of the recipient, wherein the administration is performed at least 7 days before the transplantation.

* * * * *